United States Patent [19]

Urano et al.

[11] Patent Number: 5,200,552
[45] Date of Patent: Apr. 6, 1993

[54] POLYMERIZABLE SUBSTITUTED AMIDE COMPOUND, POLYMER OBTAINED THEREFROM AND NONLINEAR OPTICAL MATERIAL USING THE SAME

[75] Inventors: Satoshi Urano, Tsuzuki; Noriyuki Tsuboniwa, Higashiosaka; Tetsuji Kawakami, Katano; Katsuya Wakita, Nara, all of Japan

[73] Assignees: Nippon Paint Co., Ltd.; Matsushita Electric Industrial Co., Ltd., both of Osaka, Japan

[21] Appl. No.: 765,513

[22] Filed: Sep. 25, 1991

[30] Foreign Application Priority Data

Sep. 25, 1990 [JP] Japan .................................. 2-256040

[51] Int. Cl.[5] .................. C07C 271/18; C07C 275/30
[52] U.S. Cl. ........................................ 560/163; 564/46
[58] Field of Search ................... 560/165, 163; 564/46

[56] References Cited

U.S. PATENT DOCUMENTS 4,237,166 1/1990 Williams et al. .................... 424/310
4,935,413 6/1990 Urano et al. ......................... 514/178

FOREIGN PATENT DOCUMENTS 0177122 4/1986 European Pat. Off. .

OTHER PUBLICATIONS

Leiser, T. et al. (1951) Berichte 84, 4–12.

*Primary Examiner*—Joseph L. Schofer
*Assistant Examiner*—M. Nagumo
*Attorney, Agent, or Firm*—Wenderoth, Lind & Ponack

[57] ABSTRACT

The present invention provides novel polymerizable substituted amide compound which are derived from the isocyanate compounds and which are useful in the preparation of nonlinear optical materials. The polymerizable substituted amide compounds of the present invention are represented by the formula;

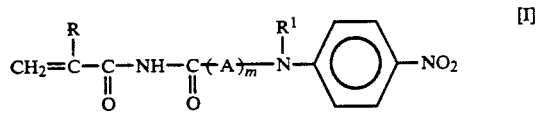

wherein R and $R^1$ respectively represent a hydrogen atom or a lower alkyl group, A represents $-X-(CH_2)_n-$ in which X represents an oxygen atom or $-NH-$ and n is an integer of 1 to 6, and m shows 0 or 1. The present invention also provides a homo- or co-polymer derived from the polymerizable substituted amide compound. The present invention further provides a nonlinear optical composition containing the homo- or co-polymer.

5 Claims, No Drawings

POLYMERIZABLE SUBSTITUTED AMIDE COMPOUND, POLYMER OBTAINED THEREFROM AND NONLINEAR OPTICAL MATERIAL USING THE SAME

FIELD OF THE INVENTION

The present invention relates to a polymerizable substituted amide compound, a homo- or co-polymer obtained therefrom and an application thereof.

BACKGROUND OF THE INVENTION

Compounds having an isocyanate group are extensively used in the field of polymer chemistry due to the excellent reactivity of the isocyanate group therein. Especially, compounds having both a polymerizable unsaturated group and an isocyanate group in their molecules have a high possibility of being usable in various industrial fields, because those two functional groups can respectively participate in various reactions with different reaction mechanisms. One of the compounds provided from this viewpoint is an isocyanate compound of the formula:

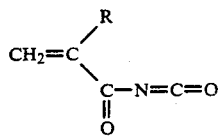
[A]

wherein R is hydrogen atom or lower alkyl group (e.g. methyl ethyl) (Japanese Patent Application (unexamined) No. 115557/1985).

Many derivatives of the above compounds are also proposed in EP-A 85304739.7. They are useful in the field of coating or plastics.

SUMMARY OF THE INVENTION

The present invention provides novel polymerizable substituted amide compounds which are derived from the isocyanate compounds of formula A and which are useful in preparation of nonlinear optical materials. The polymerizable substituted amide compounds of the present invention are represented by the formula;

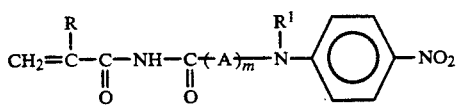
[I]

wherein R and $R^1$ respectively represent a hydrogen atom or a lower alkyl group, A represents —X—(CH$_2$)$_n$— in which X represents an oxygen atom or —NH— and n is an integer of 1 to 6, and m shows 0 or 1.

The present invention also provides a homo- or co-polymer derived from the polymerizable substituted amide compound.

The present invention further provides a nonlinear optical composition containing the homo- co-polymer.

DETAILED DESCRIPTION OF THE INVENTION

In the formula, [I] the lower alkyl group of R and $R^1$ preferably includes an alkyl having 1 to 6 carbon atoms, such as methyl, ethyl, propyl, butyl, hexyl and the like.

The substituted amide compounds [I] of the present invention may be prepared by reacting a isocyanate compound of the formula A with an amine [II] represented by the formula:

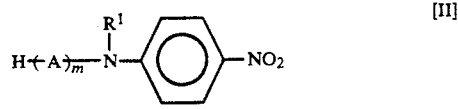
[II]

wherein in the compounds of formula A, $R^1$ and m are the same as mentioned above. Typical examples of the amine compound [II] are anilines, such as p-nitroaniline, N-methyl-p-nitroaniline and N-ethyl-p-nitroaniline; 2-[N-(p-nitrophenyl)-N-lower alkyl]aminoalkanols, such as 2-[N-(p-nitrophenyl)-N-methyl]aminoethanol, 2-[N-(p-nitrophenyl)-N-ethyl]aminoethanol, 2-[N-(p-nitrophenyl)-N-propyl]aminoethanol, 2-[N-(p-nitrophenyl)-N-butyl]aminoethanol, 2-[N-(p-nitrophenyl)-N-methyl]aminopropanol, 2-[(p-nitrophenyl)-N-ethyl]amino]aminopropanol, 2-[N-p-nitrophenyl)-N-butyl]aminobutanol and 2-[N-(p-nitrophenyl)-N-methyl]aminohexanol; and the like. The amine compound [II] can be prepared by a conventional method, for example alkylating p-nitroaniline. Some of the amine compounds [II] are commercially available.

In the preparation of the polymerizable substituted amide compound [I], the isocyanate compound [A] is reacted with the amine compound [II] at a stoichiometric amount ratio, but in general the amine compound [II] is employed in an amount of 0.5 to 5 mol base on one mol of the isocyanate compound [A]. The reaction is generally conductive in the presence of a solvent, i.e. an inert solvent. Examples of the solvent are aliphatic hydrocarbons, such as pentane, hexane and heptane; aromatic hydrocarbons, such as benzene, toluene and xylene; alicyclic hydrocarbons, such as cyclohexane, methylcyclohexane and decalin; petroleum solvents, such as petroleum ether and petroleum benzine; halogenated hydrocarbons, such as tetrachloro carbon, chloroform and 1,2-dichloroethane; ethers, such as ethyl ether, isopropyl ether, anisole, dioxane and tetrahydrofuran; ketones, such as acetone, methyl ethyl ketone, methyl isobutyl ketone, cyclohexanone, acetophenone and isophorone; ester, such as ethyl acetate and butyl acetate; acetonitrile; dimethylformamide; dimethylsulfoxide; mixtures thereof; and the like.

Since the reaction between the isocyanate compound [A] and the amine compound [II] proceeds rapidly, it is not always necessary to add a catalyst to the reaction system. If a catalyst is employed, a tin containing catalyst or an amine catalyst is preferred. A polymerization inhibitor may be added to the reaction system. Examples of the polymerization inhibitors are hydroquinone, p-methoxyphenol, 2,6-di-t-butyl-4-methylphenol, 4-t-butylcatechol, bisdihydroybenzylbenzene, 2,2-methylenebis(6-t-butyl-3-methylphenol), 4,4-butylidenebis(6-t-butyl-3-methylphenol), 4,4'-thiobis(6-t-butyl-3-methylphenol), p-nitrosophenol, diisopropylxanthogenesulfide, N-nitrosophenylhydroxyamine ammonium salt, 1,1-diphenyl-2-picrylhydrazil, 1,2,5-triphenylpherdazil, 2,6-di-t-butyl-alpha-(3,5-di-t-butyl-4-oxo-2,5-cyclohexadiene-1-ilidene)p-trioxy, 2,2,6,6-tetramethyl-4-piperidone-1-oxy, dithibenzoylsulfide, p,p'-ditolyltrisulfide, dibenzyltetrasulfide, tetraethylthiuramdifulfide and the like.

The reaction is preferably conducted in a dry atmosphere. The reaction temperature and reaction time are not limited, but preferably the reaction is conducted at a temperature of −10° to 15° C.

After the completion of the reaction, the reaction mixture is generally purified by distillation, followed by recrystallization or column chromatography to obtain the polymerizable substituted amide compound of the present invention.

The resultant polymerizable substituted amide compound has a polymerizable group therein and can produce a homo- or co-polymer. The polymer may be prepared by polymerizing the amide compound, if necessary with a copolymerizable monomer. Polymerization is generally conducted in the presence of a polymerization initiator. Typical examples of the polymerization initiatiors are azo compounds, such as azobisisobutylonitrile, 2,2-azobis-2,4-dimethylvaleronitrile, azobiscyclohexanecarbonitrile and 2-cyano-2-propylazoformamide; peroxides, such as alkyl perbenzoate, benzoyl peroxide or derivatives therefrom, di-t-butyl peroxide and cumene hydroperoxide; and the like. The peroxide initiators may be combined with reducing agents to form redox initiators. The amount of the polymerization initiator is 0.05 to 10 parts by weight, based on 100 parts by weight of the total monomer. Typical examples of the copolymerizable monomers are unsaturated organic acids, such as acrylic acid, methacrylic acid, maleic acid and itaconic acid; unsaturated amides, such as acrylamide, N-methylacrylamide, N-propylacrylamide, N-t-butylacrylamide, N,N-dimethylacrylamide, N,N-diethylacrylamide, methacrylamide, N-(p-methoxyphenyl)methacrylamide and N-(4'-nitro-4-stilbenyl)methacrylamide; mono- or di-olefins, such as styrene, alpha-methylstyrene, alpha-ethylstyrene, isobutylene, 2-methyl-butene-1, 2-methyl-pentene-1, 2,3-dimethyl-butene-1, 2,3-dimethyl-pentene-1, 2,4-dimethyl-pentene-1, 2,3,3-trimethyl-heptene-1, 2,3,3-trimethyl-heptene-1, 2,3-dimethyl-hexene-1, 2,4-dimethyl-hexene-1, 2,5-dimethyl-hexene-1, 2-methyl-3-ethyl-pentene-1, 2,3,3-trimethyl-pentene-1, 2,3,4-trimethyl-pentene-1, 2,3,4-trimethyl-pentene-1, 2-methyl-octene-1, 2,6-dimethyl-octene-1, 2,3-dimethyl-decene-1, 2-methyl-nonadecene-1, ethylene, propylene, butylene, amylene, hexylene, butadiene-1,3 and isoprene; halogenated mono- or di-olefins, such as alpha-chlorostyrene, alpha-bromostyrene, 2,5-dichlorostyrene, 2,5-dibromostyrene, 3,4-dichlorostyrene, o-, m- or p-fluorostyrene, 2,6-dichlorostyrene, 2,6-difluorostyrene, 3-fluoro-4-chlorostyrene, 3-chloro-4-fluorostyrene, 2,4,5-trichlorostyrene, dichloromonofluorostyrene, 2-chloropropene, 2-chlorobutene, 2-chloropenetene, 2-chlorohexene, 2-chlorobutene, 2-bromobutene, 2-bromoheptene, 2-fluorohexene, 2-fluorobutene, 2-iodopropene, 2-iodopentene, 4-bromoheptene, 4-chloroheptene, 4-fluoroheptene, cis- or trans-1,2-dichloroethylene, 1,2-dibromoethylene, 1,2-difluoroethylene, 1,2-diiodoethylene, chloroethylene (vinyl chloride), 1,1-dichloroethylene (vinylidene chloride), bromoethylene, fluoroethylene, iodoethylene, 1,1-dibromoethylene, 1,1-difluoroethylene, 1,1-diiodethylene, 1,1,2-trifluoroethylene and chlorobutadiene; organic or inorganic acid esters, such as vinyl acetate, vinyl propionate, vinyl butylate, vinyl isobutylate, vinyl valerate, vinyl caproate, vinyl enanthate, vinyl benzoate, vinyl toluate, vinyl-p-chloro benzoate, vinyl-o-chloro benzoate, vinyl-p-methoxy benzoate, vinyl-p-ethoxy benzoate, methyl methacrylate, ethyl methacrylate, propyl methacrylate, butyl methacrylate, amyl methacrylate, hexyl methacrylate, heptyl methacrylate, octyl methacrylate, decyl methacrylate, methyl crotonate, ethyl tiglate, methyl acrylate, ethyl acrylate, propyl acrylate, isopropyl acrylate, butyl acrylate, butyl acrylate, isobutyl acrylate, amyl acrylate, hexyl acrylate, 2-ethylhexyl acrylate, heptyl acrylate, octyl acrylate, allyl chloride, allyl cyanide, allyl bromide, allyl fluoride, allyl iodide, allyl chloride carbonate, allyl nitrate, allyl thiocyanate, allyl formate, allyl acetate, acetate propionate, allyl butylate, allyl valerate, allyl caproate, methallyl chloride, methallyl cyanide decyl-alpha-chloroacrylate, methyl-alpha-cyano acrylate, ethyl-alpha-cyano acrylate, amyl-alpha-cyano acrylate, decyl-alpha-cyano acrylate, dimethyl maleate, diethyl maleate, diallyl maleate, dimethyl fumarate, diethyl fumarate, dimethallyl fumarate and diethyl glutaconate; organic nitriles, such as acrylonitrile, methacrylonitrile, ethacrylonitrile, 3-octenenitrile, crotonitrile and oleonitrile; and the like.

The polymerization may be conducted in a solvent to which an additive may be added. The solvent may be the same as listed for the preparation of the substituted amide compound [I]. Examples of the additives are chain transfer agents, and the like, The polymerization may be conducted at a temperature of 50° to 150° C.

The obtained polymer preferably has a number average molecular weight of 1,000 to 500,000. When the polymer is used as a nonlinear optical material, it is preferred that the substituted amide compound [I] of the present invention is contained in an amount of at least 5% by weight, more preferably at least 30% by weight, based on the whole monomer amount.

The homo- or co-polymer of the present invention generally has inversion symmetry and is inactive in respect to two dimensional nonlinear optical effects. It is therefore necessary to orient the nitroanilino groups by applying electric field. The application of electric field may be conducted by sandwiching a specimen between electrodes to which a voltage is applied or by corona-charging the surface of the specimen. These treatments may referred to as "poling". The applied electric field may be at least 10 KV/mm, but in order to effectively make the poling treatment at least 100 kV/mm is preferred. Since the orientation by the poling treatment does not proceed sufficiently when the polymer is solid, it is necessary to heat the polymer specimen to a glass transition temperature or near the temperature. Before the poling treatment, the polymer may be extended to promote the orientation.

In the resultant nonlinear optical material, the nitronilino group has poor relaxation of orientation because of strong hydrogen bond by urea bonds or urethane bonds, thus the material is useful for the nonlinear optical material.

The present invention also provides a nonlinear optical composition which comprises (a) the above mentioned homo- or co-polymer and (b) a π electron conjugated organic compound having both an electron donative group and an electron attractive group. The composition has two dimensional nonlinear optical effects without such orientation treatment as the poling treatment. The content of the conjugated organic compound is preferably within the range of 10 to 80% by weight, more preferably within the range of 30 to 70% by weight, based on the total amount of the composition. Typical examples of the electron donative groups are an alkoxy group, such as methoxy group; an amino group; an alkyl or aryl-substituted amino group; an hydroxyl group; an alkyl group; and aryl group; and the like. Typical examples of the electron attractive groups are a cyano group, a nitro group, a dicyanovinyl group, a tricyanovinyl group, a carbonyl group, a carboxyl group and the like. A halogen atom may be used but belongs to both types of groups because of its amphoteric properties. The two groups are attached to a π electron conjugated compound to form the component (b). Typical examples of the π electron conjugated compounds are benzene, naphthalene, anthracene, pyrene, azobenzene, stilbene and the like. Typical examples of the components (b) are nitroaniline and cyanoaniline. The nonlinear optical composition may be prepared by mixing the components (a) and (b) in the presence or absence of a solvent. The composition may be coated on a substrate by spin coating, casting and the like. The composition changes from transparent to opaque when cooled or left to stand, because crystals grow. The changed composition has the two dimension nonlinear optical effects which continue stably.

The polymerizable substituted amide compound [I] of the present invention is divided into the following three portions;

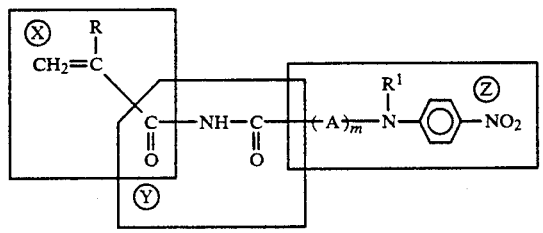

The portion (X) is a conjugated double bond structure and is easily polymerizable. Thus, the compound [I] is useful as a monomer and the obtained polymer or copolymer can be used for varnish, coating, adhesive, plastics, elastomer and the like. The compound [I] may be grafted with synthetic fibers, synthetic resins, natural polymers and the like to improve their properties.

The portion (Y) is an acyl-urethane structure which has excellent intermolecular cohesion and high possibility of forming intermolecular hydrogen bond. Accordingly, the polymer obtained therefrom has excellent properties in toughness, adhesive power, dispersibility and the like.

The portion (Z) is an amino group-containing structure where exhibits basic properties and a high reactivity to form a salt or quaternary salt. The reaction product of the compound [I] has excellent water solubility or hydrophilic properties and has good dying ability with an acid dye. It also has good reactivity or adhesion with anions and good cohesion with minus colloids, such as sludge or cellulose. The reaction product further has good electrical properties, such as static ability and electroconductivity.

The compound [I] and the reaction products therefrom have a nitrophenylamino group which has a high dipolar moment, but has poor inversion symmetry.

The compound [I] and the polymer therefrom have a p-nitro group attached to an amino nitrogen atom and therefore exhibit good secondary harmonic wave properties, which are good for nonlinear optical material in optoelectronics.

EXAMPLES

The present invention is illustrated by the following Examples which, however, are not to be construed as limiting the present invention to their details.

Preparation of The Polymerizable Substituted Amide Compound [I]

Example 1

Into 500 ml of a diethyl ether solution of 13.8 g (0.1 mol) of p-nitroaniline was added dropwise 50 ml of a diethyl ether solution of 11.1 g (0.1 mol) of methacryloyl isocyanate over about 30 minutes in an ice bath. After completion of the addition, the produced crystal was filtered and the filtrate was distilled under a reduced pressure. The yellow solid gathered from the filtration and the distillation residue was recrystallized with methyl ethyl ketone to obtain 19.7 g of 1-methacryloyl-3-(4-nitrophenyl)urea (Compound 1) which had a decomposing point of 241° to 244° C. and was yellow needle crystal.

Example 2

Into 300 ml of a methyl ethyl ketone solution of 19.7 g (0.1 mol) of 2-(N-p-nitrophenol-N-methyl)-aminoethanol was added dropwise 100 ml of a methyl ethyl ketone solution of 11.1 g (0.1 mol) of methacryloyl isocyanate over about 40 minutes in an ice bath. After completion of the addition, the produced crystal was filtered and the filtrate was distilled under a reduced pressure. The obtained yellow solid was recrystallized with methyl ethyl ketone to obtain 20.3 g of methyl-4-nitrophenylaminoethyl N-methacryloylcarbamate (Compound 2) which had a decomposing point of 127° to 128° C. and was yellow needle crystal.

Preparation of a Homo- and Co-Polymer of the Obtained Substituted Amide Compound Example 3

The compound 2 obtained in Example 2 was polymerized with methyl methacrylate (NMA) in the following compositions and conditions to obtain four polymers 1–4.

|  | Compound 2 | MMA | AIBN | DMSO |
|---|---|---|---|---|
| Composition 1 | 1.00 | — | 0.005 | 4.00 |
| Composition 2 | 0.75 | 0.25 | 0.005 | 4.00 |
| Composition 3 | 0.50 | 0.50 | 0.005 | 4.00 |
| Composition 4 | 0.25 | 0.75 | 0.005 | 4.00 |

Conditions: The composition was encapsulated in a vacuum ampoule and heated 50° C. for 12 hours and then 80° C. for 3 hours. The polymer was precipitated by ethanol and rinsed, followed by drying under vacuum.

AIBN: Azobisisobutylonitrile
DMSO: Dimethylsulfoxide

Example 4

The polymer 3 obtained in Example 3 was dissolved in tetrahydrofuran and spin-coated on a glass plate having a thickness of 0.15 mm to form a one micron layer. The coated plate was heated to 90° C. on a hot plate and corona-discharged by applying 6.4 kV to a tungsten wire. After 30 minutes, the hot plate was cooled to room temperature for 30 minutes while the corona discharge continued. The corona discharge was stopped thereafter.

Example 5

One part by weight of the polymer 4 obtained in Example 3 and one part by weight of 4-nitroaniline were dissolved in 8 parts by weight of tetrahydrofuran, and cast on a slide glass, followed by drying with hot air to obtain a dried film. After leaving it for a while, small crystals were produced throughout the film to surface. This is expressed as composition 1.

Example 6

The compound 1 to 2, the polymers 1-4 and the composition 1, obtained in Examples 1, 2, 3 and 5, were subjected to the Kurtz' powder method (J. Appl. Phys. 39,3798 (1968), by S. K. Kurtz, et al.) in which the occurrence of secondary harmonic wave (SHG) by YAG laser light (1,064 nm) was determined. A small amount of SHG was observed with the compounds 1 and 2, but no SHG was observed with the polymers 1-4. The composition 1 showed strong SHG as much as 25 times that of urea.

Example 7

The specimen obtained in Example 4 was irradiated by YAG laser light (1,064 nm) and the secondary harmonic wave at the opposite side of the irradiation was observed.

When the polarizing area of the YAG laser light was equal to the incident area, the secondary harmonic wave was maximum when the incident angle was about 60°, but is was not so strong because the light path length was small. However, the same observation was conducted after one day, 30 days and 90 days, but no substantial change was observed.

What is claimed is:

1. A polymerizable substituted amide compound represented by the formula;

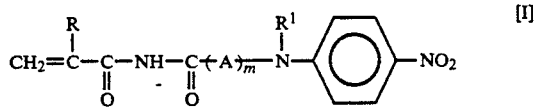

wherein R and $R^1$ respectively represent a hydrogen atom or a lower alkyl group, A represents $-X-(CH_2)_n-$ in which X represents an oxygen atom or $-NH-$ and n is an integer of 1 to 6, and m is 0 or 1.

2. The polymerizable substituted amide compound according to claim 1 wherein said lower alkyl group of R and $R^1$ has 1 to 6 carbon atoms.

3. The polymerizable substituted amide compound according to claim 1 wherein said lower alkyl group is methyl, ethyl, propyl, butyl or hexyl.

4. 1-Methacryloyl-3-(4-nitrophenyl) urea.

5. Methyl-4-nitrophenylaminoethyl N-methacryloyl-carbamate.